United States Patent [19]

Weidenbach et al.

[11] Patent Number: 4,665,025

[45] Date of Patent: May 12, 1987

[54] PROCESS FOR THE PREPARATION OF ISOGLUCOSE

[75] Inventors: Guenter Weidenbach, Hanover; Dirk Bonse, Lehrte/Arpke; Boris Meyer, Hanover, all of Fed. Rep. of Germany

[73] Assignee: Kali-Chemie Aktiengesellschaft, Hanover, Fed. Rep. of Germany

[21] Appl. No.: 694,974

[22] Filed: Jan. 25, 1985

[30] Foreign Application Priority Data

Feb. 13, 1984 [DE] Fed. Rep. of Germany ....... 3405035

[51] Int. Cl.[4] ...................... C12P 19/24; C12N 11/14
[52] U.S. Cl. ...................................... 435/94; 127/30; 127/46.1; 435/176
[58] Field of Search ........................ 127/30, 42, 46.1; 435/94, 176, 234, 887

[56] References Cited

U.S. PATENT DOCUMENTS

| | | | |
|---|---|---|---|
| 3,910,821 | 10/1975 | Cory | 127/42 X |
| 4,230,803 | 10/1980 | Weidenbach et al. | 435/176 |
| 4,288,548 | 9/1981 | Barrett et al. | 435/94 |
| 4,310,628 | 1/1982 | Leiser | 435/94 |
| 4,381,345 | 4/1983 | Rohrbach et al. | 127/46.1 X |
| 4,382,121 | 5/1983 | Rohrbach et al. | 127/30 X |
| 4,533,633 | 8/1985 | Weidenbach et al. | 435/176 X |

FOREIGN PATENT DOCUMENTS

| | | | |
|---|---|---|---|
| 2726188 | 8/1978 | Fed. Rep. of Germany | 127/46.1 |
| 3148603 | 7/1983 | Fed. Rep. of Germany | 127/46.1 |

*Primary Examiner*—Richard V. Fisher
*Assistant Examiner*—W. Gary Jones
*Attorney, Agent, or Firm*—Schwartz, Jeffery, Schwaab, Mack, Blumenthal & Evans

[57] ABSTRACT

Disclosed is a process for the preparation of a solution containing glucose and fructose (isoglucose) by the conversion of a glucose-containing solution on a catalyst having glucose isomerase activity and produced on the basis of a $SiO_2$ carrier. The productivity of the catalyst may be significantly increased by the addition of $SiO_2$ to the glucose solution, and the catalyst according to the present invention is not damaged by temporary process shutdowns.

16 Claims, 3 Drawing Figures

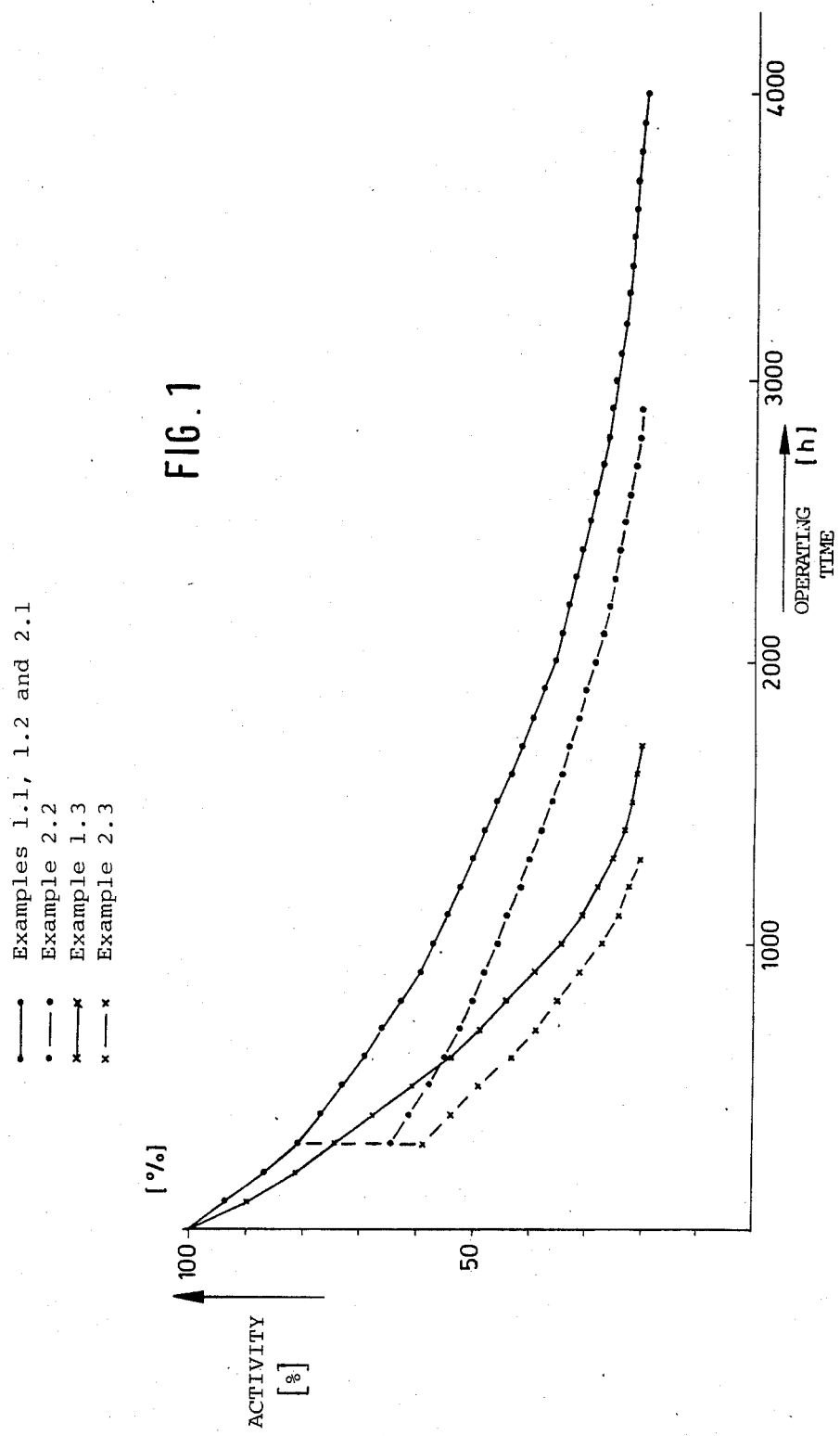

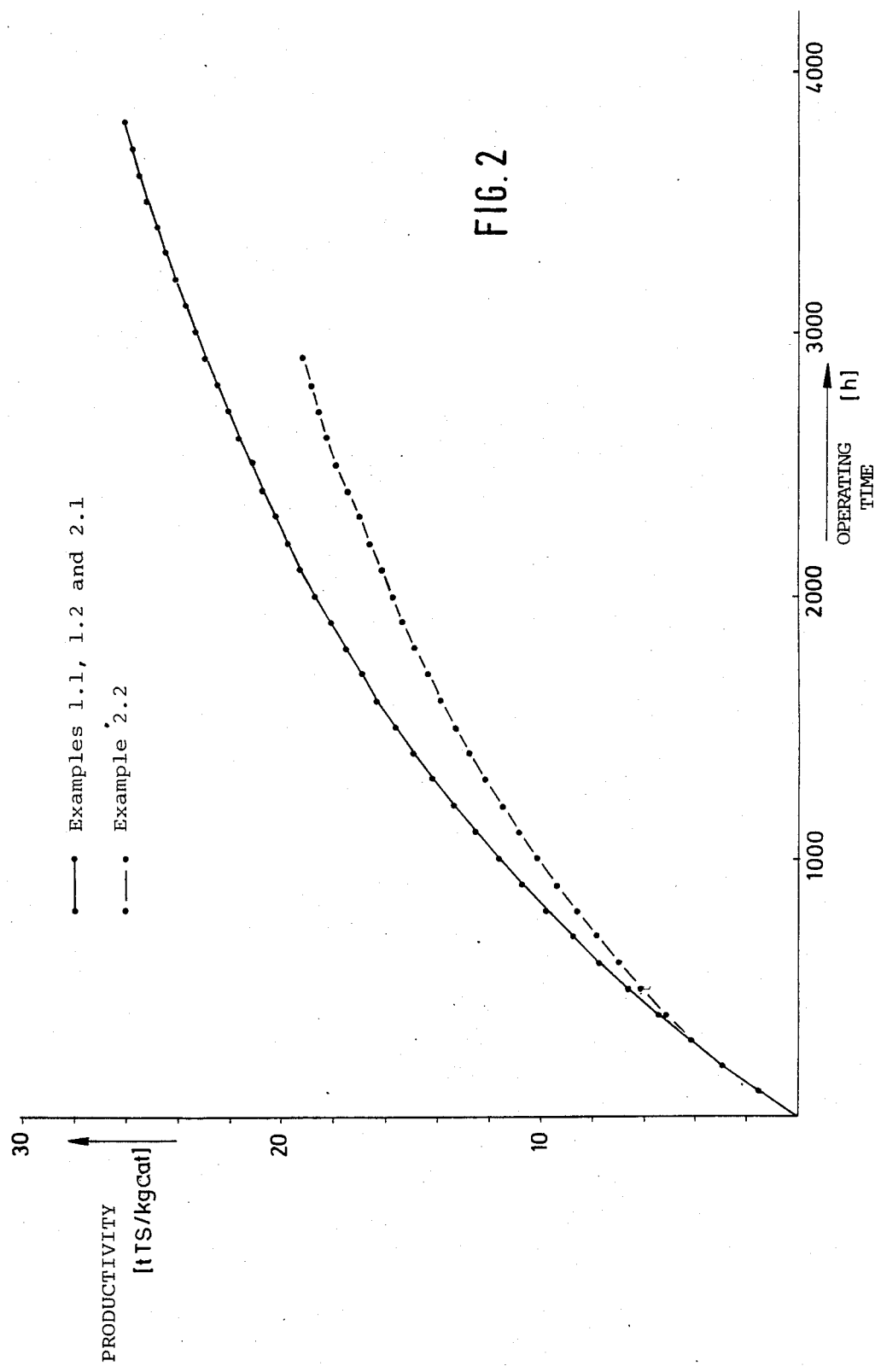

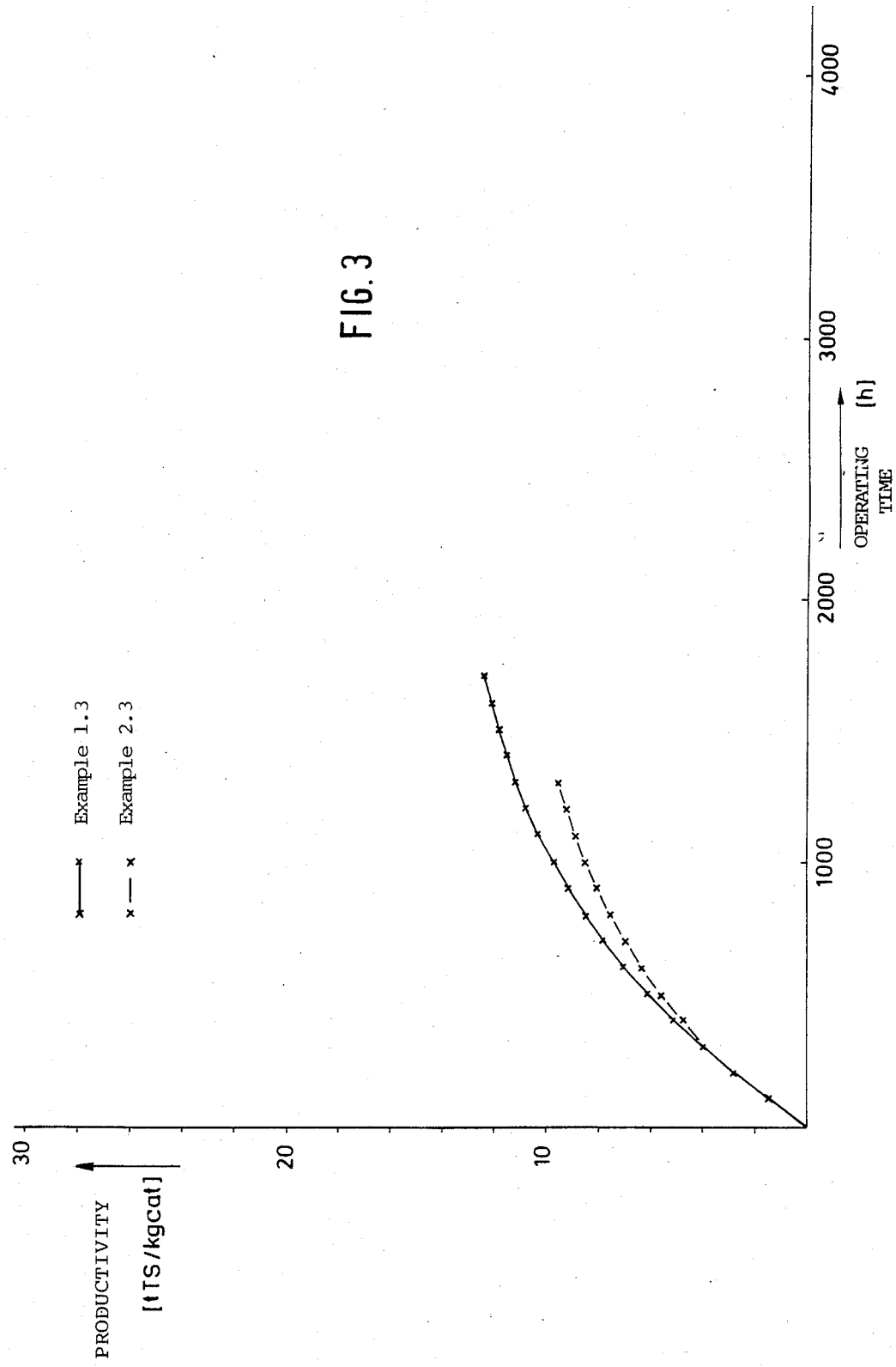

PROCESS FOR THE PREPARATION OF ISOGLUCOSE

BACKGROUND OF THE INVENTION

The present invention relates to a process for the preparation of a solution containing glucose and fructose by the conversion of a glucose containing solution in the presence of a catalyst having glucose isomerase activity which is prepared based on a $SiO_2$ carrier.

German Pat. No. 31 48 603 discloses a process of this type wherein the productivity of known supported catalysts, which have glucose isomerase activity and which are prepared on the basis of a $SiO_2$ carrier, may be considerably enhanced by bringing the glucose containing solution, prior to conversion on the supported catalyst, into contact with molded bodies of $SiO_2$ or alumosilicate.

SUMMARY OF THE INVENTION

It is therefore an object of the present invention to provide a process for the preparation of isoglucose which uses a $SiO_2$ supported catalyst having glucose isomerase activity with increased productivity compared to known catalysts.

It is another object of the present invention to provide a process as above, wherein the activity of the catalyst is unaffected by an interruption of the process.

Still another object of the present invention is to provide a process as above, wherein it is unnecessary to provide rapid cooling of the catalyst during interruption of the process.

In accomplishing the foregoing objects, there has been provided in accordance with one aspect of the present invention a process for the continuous preparation of a solution containing glucose and fructose by the conversion of a glucose-containing solution in the presence of a catalyst having glucose isomerase activity, comprising the steps of adding a water-soluble form of $SiO_2$ to the solution, introducing the solution into a reactor containing a $SiO_2$-supported catalyst, and removing an effluent stream of the glucose/fructose-containing solution. In addition, the reactor effluent may be monitored for its fructose content and the process regulated such that the fructose weight percent in the effluent remains approximately constant. Also the space velocity of the reaction process can be adjusted to maintain an approximately constant degree of isomerization.

Further objects, features and advantages of the present invention will become apparent from the detailed description of preferred embodiments which follows, when considered together with the attached figures of drawing.

BRIEF DESCRIPTION OF THE DRAWINGS

In the drawings:

FIG. 1 shows the reduction in catalytic activity corresponding to each of the Examples herein;

FIGS. 2 and 3 illustrate the variation in catalytic productivity as a function of operating time.

DETAILED DESCRIPTION OF PREFERRED EMBODIMENTS

The present invention provides a process for the preparation of a solution containing glucose and fructose by the conversion of a glucose-containing solution on a catalyst having glucose isomerase activity produced on the basis of a $SiO_2$ carrier, wherein $SiO_2$ is added to the glucose solution. The terms "catalysts prepared on the basis of $SiO_2$ carriers and having glucose isomerase activity" and "known $SiO_2$ supported catalysts having glucose isomerase activity" are intended to signify catalysts wherein glucose isomerase is worked into or applied to a carrier based on $SiO_2$, for example, by adsorptive or covalent bonding or cross linking of the enzyme to a porous silica gel. Preferably, the terms are intended to signify catalysts wherein glucose isomerase is bonded to a porous silica gel by adsorptive or covalent means or is applied by cross-linking and wherein combinations of the aformentioned bonding methods may also be used. Preferred catalysts of this type are disclosed, for example, in German Pat. No. 27 26 188.

The production of the above-described process may be enhanced, in accordance with the present invention, by the addition of $SiO_2$ to the glucose-containing solution.

$SiO_2$ may be added in any form, provided that it is adequately water soluble and that foreign ions which are potentially introduced together with the $SiO_2$ into the glucose solution do not interfere with the activity of the enzyme or the subsequent utilization of the glucose-frustose solution. Alkaline metal silicates have been found to be particularly suitable.

The amount of $SiO_2$ added is not particularly critical. In order to obtain an increase in productivity of the extent contemplated by the process disclosed in German Pat. No. 31 48 603, the amount added should not be less than about 30 ppm. Optimally, between about 30 and 80 ppm $SiO_2$ are added to the glucose solution.

The addition of $SiO_2$ involves a particularly simple and cost effective process if a solution of water glass, preferably sodium water glass, is used.

With regard to the increase in productivity achieved according to the process the present invention, values are comparable to those attained by the process according to German Pat. No. 31 48 603. Surprisingly, however, the addition of $SiO_2$ in place of the preliminary contacting with molded bodies of $SiO_2$ or alumosilicate, has an advantageous effect on the stability of the catalyst during a cessation of operation. It has been found that an interruption of the process according to German Pat. No. 31 48 603 or other known processes due to a power failure or other causes results in irreversible damage to the catalyst activity if care is not taken to cool the catalyst to room temperature as rapidly as possible. In the case, for example, of a power failure, not only the pumps but also the heating device for the heating of the substrate are incapacitated. The heat capacity of the catalyst and the substrate solution surrounding it prevents the necessary rapid cooling and is sufficient to damage the catalyst. In order to prevent such damage, precautions must be taken, for example by means of emergency generators, so that upon a cessation of operations cold substrate solution may be pumped through the reactor, in order to obtain the necessary rapid cooling of the sensitive catalyst. When working according to the process of the present invention, however, such precautionary measures may be entirely eliminated.

The process according to the present invention may be operated continuously. In particular, the $SiO_2$ may be added to an aqueous solution containing glucose in a concentration of approximately 40 to 50% by weight of dry substance (DS). The solution is adjusted to a pH value appropriate for the carrier bound glucose isomerase and is heated to an isomerizing temperature suitable for the carried bound glucose isomerase. The glucose solution prepared in this manner is pumped through a reactor filled with the SiO$_2$ supported catalyst having glucose isomerase activity. The glucose/fructose solution coming from the reactor is examined continuously or at regular intervals for its fructose content, for example, by means of polarimetric analysis or High Pressure Liquid Chromatography. The space velocity (v/vh = volume of glucose solution per reactor volume occupied by the catalyst per hour), at which the catalyst is operated is adjusted so that the effluent solution, with respect to the dry substance, has a fructose content of, for example, about 42% by weight that is constant within a relatively slight variation of, for example, about ±1%. Since the catalytic activity constantly decreases as a function of operating time and in particular the operating temperature, this means that the space velocity must be steadily reduced in order to attain a constant degree of isomerization. The degree of isomerization is expressed in percent and indicates the number of fructose molecules contained in the effluent glucose-fructose solution after passing through the reactor and having been converted on the catalyst, per 100 glucose molecules contained in the initial solution. Depending on the purity and quality of the glucose used in the preparation of the glucose solution, in order to attain the aforementioned value of about 42% by weight fructose (based on dry substance) of the effluent glucose-fructose solution, the catalyst must be operated at a space velocity yielding a degree of isomerization of from approximately 44 to 47%.

If a *Streptomyces albus* glucose isomerase has been used in the preparation of the supported catalyst having glucose isomerase activity, the adjustment of the glucose solution to a pH of from approximately 7.0 to 8.5 and the heating of the glucose solution to a temperature of from approximately 55° to 65° C. has been found to be especially favorable.

Furthermore, in the case of a *Streptomyces albus* glucose isomerase, the addition of Co(II) and Mg(II) ions to the glucose solution has been found to promote isomerization. The addition of from about 0.1 to 2 ppm Co(II) and from approximately 10 to 200 ppm Mg(II), optimally in the form of their water soluble salts, such as, for example, chlorides or sulfates, has been found to be particularly advantageous.

Finally, it is advantageous to add a stabilizing amount of an antioxidant, preferably SO$_2$ to the glucose solution in a quantity of from approximately 100 to 600 ppm, preferably in the form of an alkaline metal sulfite or bisulfite.

Prior to the final use of the glucose/fructose solution which has been proposed in accordance with the present invention, it is advisable to remove any ionic component for example by means of ion exchange from the glucose/fructose solution which may be undesirable, for example, because it interferes with taste. The solution may optionally be condensed into a syrup. Commercially, such a syrup is marketed as isosyrup, isomerose or isoglucose.

The invention will become more clearly understood from the following, non-limiting examples.

EXAMPLE 1

General Example

In all of the examples, a catalyst produced according to German Pat. No. 27 26 188 was used as the "catalyst having glucose isomerase activity prepared on the basis of a SiO$_2$ carrier". In each example, 5 g of the catalyst were placed into a reactor. A glucose solution heated to 60° C. was flowed through the reactor. The space velocity (with respect to the volume of the reactor containing the catalyst) was set so that the degree of isomerization over the entire period of the operation remained constant at about 46.5%. The degree of isomerization of the outgoing substrate solution was measured by polarimetric means. In particular, the catalyst and the process are characterized by the following essential parameters:

Catalyst:

| Carrier | SiO$_2$ |
|---|---|
| Activity uptake | 9000 U/g |
| Grain size | 0.1–0.2 mm |
| Bulk density (dry) | 0.45 kg/l |

Process:

| Substrate | 45% by weight glucose in aqueous solution |
|---|---|
| Cofactors | 120 ppm Mg (II) |
| | 1 ppm Co (II) |
| | 200 ppm SO$_2$ (in the form of Na$_2$SO$_3$) |
| pH value | 7.5 |
| Substrate density | 1.2 kg/l |
| Substrate inlet temperature | 60° C. |
| Degree of isomerization | 46.5% |
| Initial space velocity | 13.0 h$^{-1}$ |

Determination of the activity of the glucose isomerase solution:

The activity of the glucose isomerase solution used n the preparation of the catalyst was determined by the Takasaki method (Y. Takasaki: Agr. Biol. Chem. Vol. 30, No. 12, 1247–1253, 1966 and Z. Dische and E. Borenfreund: J. Bio. Chem. 192, 583, 1951). One activity unit (U) is defined as the amount of the enzyme which forms 1 mg fructose under incubation conditions.

Incubation conditions:

| Temperature | 65° C. |
|---|---|
| Reaction time | 1 h |
| Substrate | 0.1 m glucose × H$_2$O (Merck 8342) in 0.05 m phosphate buffer, pH 8.0 with 0.0004 m MgSO$_4$ |

Decisive criteria of the quality of the catalysts and of the process wherein the catalyst is used are, in addition to the decrease of activity, the operating time to the residual activity of 20% of the initial activity (20% residual activity with respect to initial activity = 100% has been found to be the lower limit of the economically utilizable catalyst activity) and primarily the productivity. Productivity is defined as the amount of substrate, calculated as the dry substance in kg, which may be processed with a given degree of isomerization to a residual reactivity of 20% of the initial activity.

EXAMPLE 1.1

Example according to the invention

General Example 1 was repeated with the added condition that the glucose solution, in keeping with the invention, contained about 50 ppm $SiO_2$ in the form of a solution of sodium water glass. The results were as follows:

| | |
|---|---|
| Half life | 1300 h |
| Operating time to 20% residual activity | 3800 h |
| Productivity after 3800 h | 26,000 kg DS with 46.5% by weight fructose/1 kg catalyst |

EXAMPLE 1.2

Comparative Example according to German Pat. No. 31 48 603

General Example 1 was repeated, except that $SiO_2$ was not added to the glucose solution as according to the present invention, but the solution was pumped, prior to charging it into the reactor, through a precolumn preceding the reactor, in accordance with German Pat. No. 31 48 603. The precolumn was filled with 5 g of commercially available, spherical, water resistant, porous alumosilicate (composition approximately 97% by weight $SiO_2$ and 3% by weight $Al_2O_3$; grain size 1–2 mm; bulk density, dry, 0.7 kg/l; Type KCT-WS of Kali-Chemie AG).

The results obtained (half life value, reaction time, productivity) were identical with those of Example 1.1.

EXAMPLE 1.3

Comparative Example

This example corresponds to General Example 1, i.e. the glucose solution did not contain the addition of $SiO_2$ according to the invention and it was not passed through a precolumn filled with shaped bodies of $SiO_2$ or alumosilicate. The results were as follows:

| | |
|---|---|
| Half life | 670 h |
| Operating time to 20% residual activity | 1700 h |
| Productivity after 1700 h | 12,500 kg DS with 46.5% by weight fructose/1 kg catalyst |

EXAMPLE 2

To simulate a shutdown of the operation, Examples 1.1, 1.2 and 1.3 were repeated with the added condition that after 300 operating hours the flow of the glucose solution was interrupted without a change in the reactor temperature for 3 h. This had the following effects:

EXAMPLE 2.1

There were no changes with respect to Example 1.1.

EXAMPLE 2.2

After the resumption of the flow, the activity of the catalyst had declined from 81% to 64% of the initial activity, corresponding to a relative loss of activity of 21%. For the rest, the following final results were obtained:

| | |
|---|---|
| Half life | 800 h |
| Operating time to 20% residual activity | 2900 h |
| Productivity after 2900 h | 19,200 kg DS with 46.5% by weight fructose/1 kg catalyst |

EXAMPLE 2.3

In this example the activity of the catalyst has declined from 75% to 59% of the initial activity following the resumption of the flow, corresponding to a relative loss of activity again of 21%. Final results were as follows:

| | |
|---|---|
| Half life | 480 h |
| Operating time to 20% residual activity | 1300 h |
| Productivity after 1300 h | 9600 kg DS with 46.5% by weight fructose/1 kg catalyst |

The examples show that it is possible to obtain with the invention an increase in productivity equal to that attained according to the process disclosed in German Pat. No. 31 48 603, but that when operating in accordance with the invention, interruptions of the operation result in no damage to the catalyst activity even when the reactor temperature is held constant.

To illustrate the Examples, in the diagrams attached hereto the reduction in activity (FIG. 1) and the variation of productivity (FIGS. 2 and 3), were plotted as a function of operating time. In all of the diagrams, operating time is plotted on the abcissa in hours. On the ordinate of FIG. 1 the activity is plotted in % and on the ordinate of FIGS. 2 and 3 the productivity is plotted in t (tons) of the dry substance (DS) per kg of the catalyst. Measured values for the individual curves are shown as follows:

| | |
|---|---|
| Examples 1.1, 1.2 and 2.1: | "•———•" |
| Example 1.3: | "x———X" |
| Example 2.2: | "•  •" |
| Example 2.3: | "X  x" |

What is claimed is:

1. A process for the preparation of a solution containing glucose and fructose, comprising the steps of: adding at least about 30 ppm of $SiO_2$ in the form of a water-soluble alkali metal silicate to a glucose-containing solution, and thereafter exposing the glucose-containing solution to a catalyst having glucose isomerase activity, said catalyst being supported on a $SiO_2$ carrier.

2. A process according to claim 1, wherein $SiO_2$ is added to the glucose-containing solution in an amount ranging up to 80 ppm.

3. A process according to claim 1, wherein the $SiO_2$ is added to the glucose-containing solution in the form of water glass.

4. A process according to claim 3, wherein the $SiO_2$ is introduced to the glucose solution in the form of sodium water glass.

5. A process for the continuous preparation of a solution containing glucose and fructose by the conversion of a glucose-containing solution on a catalyst having glucose isomerase activity, comprising the steps of:

adding at least about 30 ppm of $SiO_2$ in the form of a water-soluble alkali metal silicate to said glucose-containing solution;

thereafter exposing the solution to the catalyst; and removing an effluent stream of the glucose- and fructose-containing solution.

6. A process according to claim 5, further comprising the steps of monitoring the reactor effluent for its fructose content and regulating the process such that the fructose weight percent in the effluent remains approximately constant.

7. A process according to claim 6, wherein the weight percent of fructose in the reactor effluent is about 42%.

8. A process according to claim 5, further comprising the step of adjusting the space velocity to maintain an approximately constant degree of isomerization.

9. A process according to claim 8, wherein the process is operated at a space velocity which yields a degree of isomerization of from about 44 to 47%.

10. A process according to claim 5, wherein said catalyst is prepared with the use of a *Streptomyces albus* glucose isomerase, the pH of the glucose solution is adjusted to from about 7 to 8.5, and the temperature is maintained from about 55° to 65° C.

11. A process according to claim 5, further comprising the step of adding Co(II) and Mg(II) ions to the glucose solution.

12. A process according to claim 11, wherein from about 0.1 to 2 ppm Co(II) and from about 10 to 200 ppm Mg(II) are added in the form of water-soluble salts.

13. A process according to claim 12, wherein said salts comprise chlorides or sulfates.

14. A process according to claim 5, further comprising the addition of an antioxidant.

15. A process according to claim 14, wherein the antioxidant comprises from about 100 to 600 ppm of $SO_2$, added in the form of an alkali metal sulfite or bisulfite.

16. A process according to claim 5, further comprising the step of purifying the glucose/fructose solution of ionic components.

* * * * *